(12) United States Patent
Haimi (10) Patent No.: US 10,918,797 B2
(45) Date of Patent: Feb. 16, 2021

(54) SYRINGE FOR DIRECT USE WITH MEDICAL AMPOULES AND VIALS

(71) Applicant: S-VIAL Ltd., Or Akiva (IL)

(72) Inventor: Shlomo Uri Haimi, Or Akiva (IL)

(73) Assignee: S-VIAL Ltd., Or Akiva (IL)

( * ) Notice: Subject to any disclaimer, the term of this patent is extended or adjusted under 35 U.S.C. 154(b) by 177 days.

(21) Appl. No.: 15/950,203

(22) Filed: Apr. 11, 2018

(65) Prior Publication Data

US 2018/0228978 A1 Aug. 16, 2018

Related U.S. Application Data

(63) Continuation of application No. 14/817,615, filed on Aug. 4, 2015, now abandoned.

(51) Int. Cl.
*A61M 5/24* (2006.01)
*A61M 5/19* (2006.01)

(52) U.S. Cl.
CPC ............. *A61M 5/24* (2013.01); *A61M 5/19* (2013.01); *A61M 5/2429* (2013.01);
(Continued)

(58) Field of Classification Search
CPC .... A61M 5/2429; A61M 5/24; A61M 5/2448; A61M 5/28; A61M 5/2422; A61M 5/2455; A61M 5/285; A61M 5/31511; A61M 2005/31598; A61M 2005/2403; A61M 2005/2481; A61M 2005/2407; A61M 5/002; A61M 5/3202; A61M 5/003; A61M 2005/004; A61M 2005/005; B67B 7/92; Y10T 225/30; A61B 2090/037;
(Continued)

(56) References Cited

U.S. PATENT DOCUMENTS

| | | | |
|---|---|---|---|
| 3,330,280 A | 7/1967 | Ogle | |
| 3,506,006 A * | 4/1970 | Lange, Jr. | ............ A61M 5/24 604/190 |

(Continued)

FOREIGN PATENT DOCUMENTS

| | | |
|---|---|---|
| EP | 1685865 | 8/2006 |
| WO | 2000053241 | 9/2000 |

(Continued)

*Primary Examiner* — Kevin C Sirmons
*Assistant Examiner* — Alexandra Lalonde
(74) *Attorney, Agent, or Firm* — Mark M. Friedman (57) ABSTRACT

A kit for the direct use of a variety of medical ampoules of differing sizes, with a syringe, the kit having: a syringe body; a syringe plunger having a hollow interior volume; and a plurality of ampoule interface elements, each one being interchangeably received within the hollow interior volume and configured for deployment between an outer surface of the medical ampoule and a surface of the hollow interior volume so as to hold the medical ampoule therein, each of the plurality of ampoule interface elements having an outside diameter sized to fit an inside diameter of the hollow interior volume, wherein a first of the ampoule interface elements has an inside diameter for receiving a medical ampoule of a first size, and a second of the ampoule interface elements has an inside diameter different from the first inside diameter for receiving a medical ampoule of a second size.

10 Claims, 6 Drawing Sheets

(52) U.S. Cl.
CPC ... *A61M 5/2455* (2013.01); *A61M 2005/2403* (2013.01); *A61M 2005/2433* (2013.01); *A61M 2005/2485* (2013.01)

(58) Field of Classification Search
CPC .... A61F 2002/30561; A61F 2250/0071; B01F 15/0205; A61J 1/065; A61J 1/2089; A61J 1/2096; A61J 1/06; A61J 1/03
USPC .................................. 604/193; 206/571, 483
See application file for complete search history.

(56) References Cited

U.S. PATENT DOCUMENTS

| | | | |
|---|---|---|---|
| 4,267,836 A * | 5/1981 | Whitney | A61M 5/14546 604/135 |
| 5,067,948 A | 11/1991 | Haber et al. | |
| 5,129,566 A | 7/1992 | Ogden et al. | |
| 5,306,277 A * | 4/1994 | Bryant | A61B 17/8833 604/187 |
| 8,231,567 B2 | 7/2012 | Tennican et al. | |
| 2010/0301089 A1 | 12/2010 | Mueller | |
| 2014/0100532 A1 | 4/2014 | Tennican et al. | |

FOREIGN PATENT DOCUMENTS

| | | |
|---|---|---|
| WO | 0100261 | 1/2001 |
| WO | 2002072173 | 9/2002 |

* cited by examiner

SYRINGE FOR DIRECT USE WITH MEDICAL AMPOULES AND VIALS

FIELD AND BACKGROUND OF THE INVENTION

The present invention is syringe for direct use with medical ampoules and vials and a method for its use.

SUMMARY OF THE INVENTION

The present invention is a syringe for direct use with medical ampoules and medical vials that contain medicine, cosmetics and the like.

According to the teachings of the present invention there is provided, a syringe for use with a medical ampoule, the syringe comprising: (a) a syringe body; (b) a syringe plunger having a hollow interior volume which is open at one end; and (c) an ampoule interface element configured for deployment between an outer surface of the ampoule and the surface of the hollow interior volume so as to hold the medical ampoule in the hollow interior volume.

According to the teachings of the present invention the ampoule interface is configured for deployment on the ampoule and the hollow interior volume is configured to accept insertion of the ampoule with the ampoule interface deployed thereon.

According to the teachings of the present invention the ampoule interface has an inside diameter equal to an outside diameter of the ampoule and the ampoule interface has an outside diameter equal to an inside diameter of the hollow interior volume of the syringe plunger.

According to the teachings of the present invention the inside diameter of the hollow interior volume of the syringe plunger varies along a length so as to increase friction between the outside diameter of the ampoule interface and the inside diameter of the hollow interior volume.

According to the teachings of the present invention the ampoule interface is breakable and configured for use with a breaking ampoule such that the ampoule interface is deployed on the breaking ampoule prior to breaking wherein the ampoule interface aids in a breaking process of the ampoule thereby providing added protection to a user during the breaking process.

There is also provided according to the teaching of the present invention an ampoule interface element for use holding a medical ampoule in a hollow interior volume of a syringe plunger, the ampoule interface comprising an inside surface configured to interact with an outside surface of the ampoule and an outside surface configured to interact with an inside surface of the hollow interior volume of the syringe plunger so as to hold the ampoule inside the hollow interior volume.

According to the teachings of the present invention the ampoule interface is configured for deployment on the medical ampoule prior to insertion of the ampoule, with the ampoule interface deployed thereon, into the hollow interior volume.

According to the teachings of the present invention the ampoule interface is configure with an inside diameter equal to an outside diameter of the medical ampoule and the ampoule interface has an outside diameter equal to an inside diameter of the hollow interior volume.

According to the teachings of the present invention the ampoule interface is breakable and configured for use with breaking ampoules such that the ampoule interface is deployed on the breaking ampoule prior at breaking, wherein the ampoule interface aids in a breaking process of the ampoule thereby providing added protection to a user during the breaking process.

There is also provided according to the teaching of the present invention a method of deploying a medical ampoule in a syringe, the method comprising: (a) providing a syringe body; (b) providing a syringe plunger having a hollow interior volume which is open at one end; and (c) providing an ampoule interface element configured for deployment between an outer surface of the medical ampoule and a surface of the hollow interior volume so as to hold the medical ampoule in the hollow interior volume; (d) deployment of the ampoule interface element; and (e) insertion of the medical ampoule into the hollow interior volume such that the ampoule interface element holds the medical ampoule therein.

According to the teachings of the present invention, there is also provided providing the ampoule interface having an inside diameter equal to an outside diameter of the ampoule and the ampoule interface having an outside diameter equal to an inside diameter of the hollow interior volume of the syringe plunger.

According to the teachings of the present invention, there is also provided providing the ampoule interface as breakable and configured for use with breaking ampoules and further including the steps of: (f) deploying the ampoule interface on the breaking ampoule prior at breaking; (g) breaking the ampoule wherein the ampoule interface aids in a breaking process of the ampoule thereby providing added protection to a user during the breaking process; and (h) inserting a medicine containing portion of the now broken ampoule into the hollow interior volume with a portion of the ampoule interface still deployed thereon.

There is also provided according to the teaching of the present invention a syringe for use with a medical vial, the syringe comprising: (a) a syringe body; (b) a syringe plunger having a hollow interior volume which is open at one end; and (c) a vial interface element configured for deployment between an outer surface of the medical vial and a surface of the hollow interior volume so as to hold the medical vial in the hollow interior volume the vial.

According to the teachings of the present invention the vial interface is configured for deployment on the medical vial and the hollow interior volume is configured to accept insertion of the medical vial with the vial interface element deployed thereon.

According to the teachings of the present invention the vial interface element has an inside diameter equal to an outside diameter of the medical vial and the vial interface element has an outside diameter equal to an inside diameter of the hollow interior volume as to hold the medical vial, upon which the vial interface element is deployed, in the hollow interior volume.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a syringe for direct use with medical ampoules and vials that includes an ampoule sheath and in which the syringe plunger is configured to accept insertion of the ampoule with an ampoule sheath deployed thereon.

The principles and operation of a syringe for direct use with medical ampoules and vials according to the present invention may be better understood with reference to the drawings and the accompanying description.

By way of introduction, it will be understood that numerous devices are in use today to aid users in safely breaking breakable medical ampoules. Likewise, there are syringe devices for use in extracting medicines from the broken ampoule. The syringe of the present invention comes to address both of these issues in a single device.

Figure 1A:
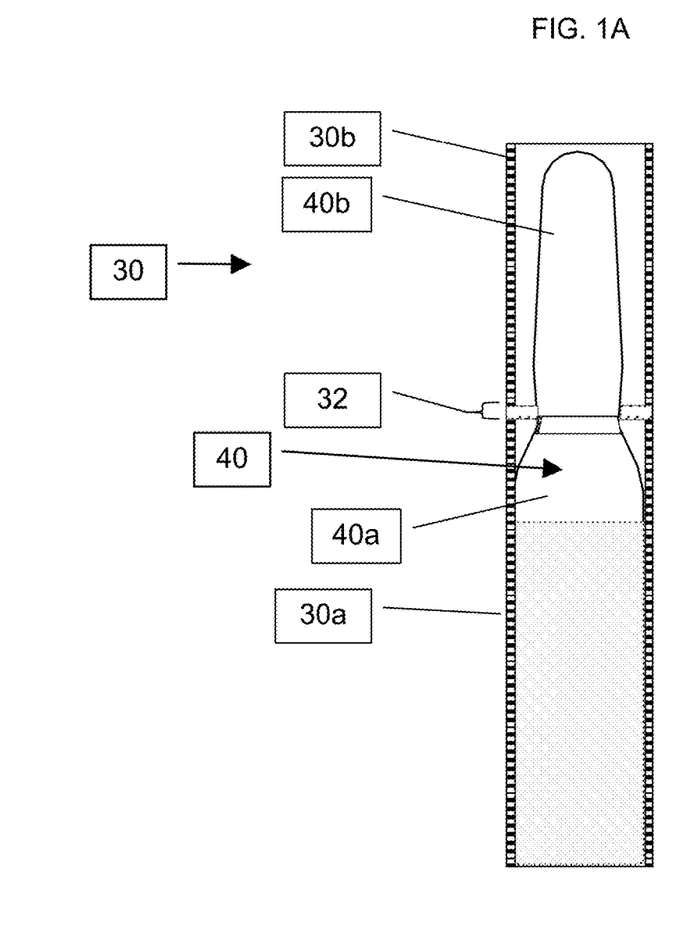
FIG. 1A is a longitudinal section view of a first preferred embodiment of an ampoule sheath constructed and operational according to the teaching of the present invention, shown here after deployment on a breaking ampoule but prior to breaking.

Referring now to the drawings, FIG. 1A illustrates a first preferred embodiment of the ampoule sheath 30 of the present invention that is directed to use with a breaking ampoule 40.

Figure 1B:
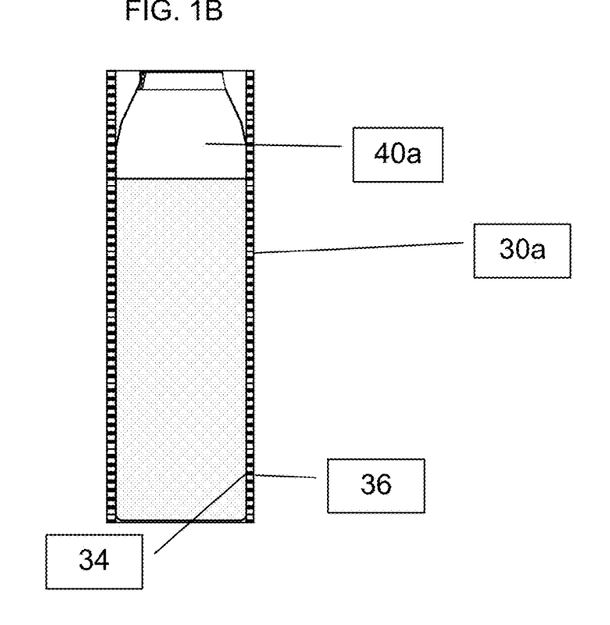
FIG. 1B is a longitudinal section view of the ampoule sheath of FIG. 1A, shown here is the portion of the ampoule sheath deployed on the ampoule after breaking the ampoule and the ampoule sheath.
Figure 1C:
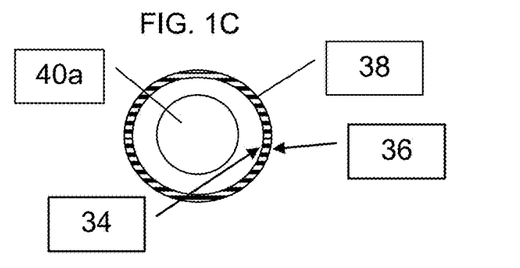
FIG. 1C is a top view of the ampoule and the ampoule sheath for FIG. 1B.

As illustrated in FIGS. 1A, 1B and 1C, the ampoule sheath 30 of the present invention is deployed on breakable ampoule 40 such that the bottom portion 30*a* of the ampoule sheath 30 is deployed on the medicine containing bottom portion 40*a* of the ampoule and top portion 30*b* of the ampoule sheath 30 is deployed on the top breakaway portion 40*b* of the ampoule with the "break lines" 32 of the ampoule sheath 30 aligned with the break line of breakable ampoule 40.

FIG. 1B illustrates the bottom portion 30*a* of the ampoule sheath 30 is deployed on the medicine containing bottom portion 40*a* of the ampoule after breaking.

It will be appreciated that the ampoule sheath 30 can be fabricated from substantially any suitable material and variant embodiments may be rigid, brittle, pliable, flexible or elastic. When breaking the top off of the ampoule, the ampoule sheath 30 may be configured to break or tear along the "break line", depending on the material from which it is fabricated.

Figure 2A:
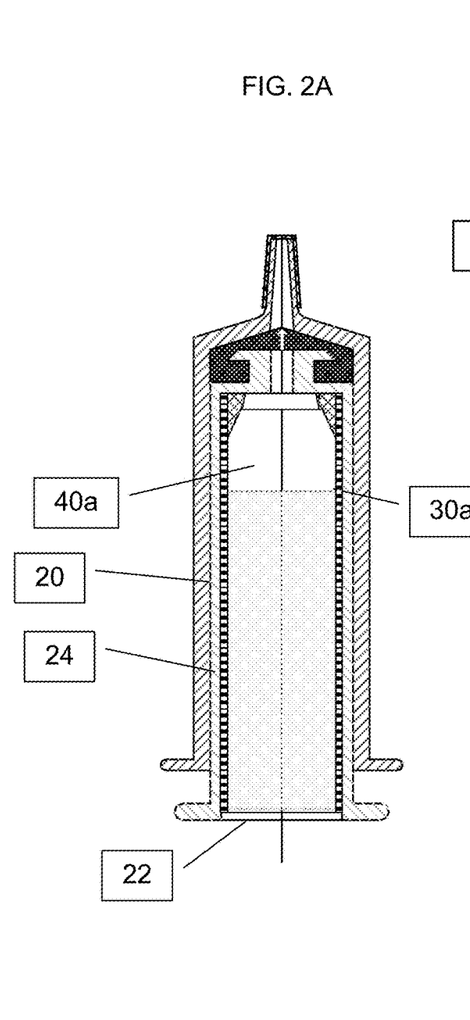
FIG. 2A is a longitudinal section view of a first preferred embodiment of a syringe constructed and operational according to the teaching of the present invention, shown here with an ampoule deployed in the plunger and the plunger deployed in the syringe body the plunger pulled out of the syringe body.
Figure 2B:
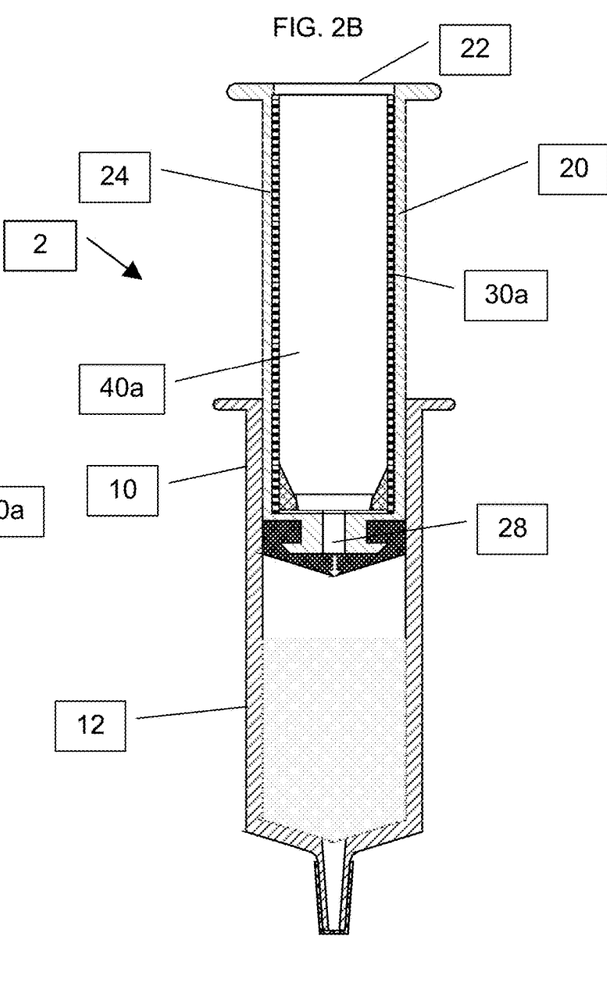
FIG. 2B is a longitudinal section view of the syringe of FIG. 2A, shown here with the plunger pulled out of the syringe body and the liquid drawn out of the ampoule and into the syringe barrel.

As illustrated in FIGS. 2*a* and 2B, Syringe 2 includes a syringe body 10 and a syringe plunger 20.

The syringe plunger 20 is configured with a hollow interior volume 24 which is open at one end 22.

Among the unique features of the present invention, as illustrated here, is the deployment of the medicine containing portion 40*a* of breaking ampoule 40 directly in the hollow volume 24 of the syringe plunger 20. Once deployed, the medicine contained in the ampoule is drawn into the barrel 12 of the syringe body 10 through passageway 28 in the syringe plunger 20 by vacuum pressure that is created when the plunger 20 is drawing out of the syringe body 10 as illustrated in FIG. 2B. The use of passages and one way valves to allow ambient air pressure into the ampoule as the liquid is drawn out is well known in the art and will not be addressed herein.

To assist in the secure deployment of the ampoule 40*a* in the hollow volume 24 of the syringe plunger 20 an ampoule sheath 30 is provided. The ampoule sheath 30, therefore, acts as an ampoule interface element deployed between an outer surface of the ampoule 40*a* and the surface of the hollow interior volume 24 so as to hold the medical ampoule 40*a* in the hollow interior volume. Additionally, but not necessarily, the ampoule sheath may provide a seal between the ampoule 40*a* in the hollow volume 24 of the syringe plunger 20.

As discussed above, the ampoule sheath 30 is configured for deployment on the ampoule prior to insertion of the ampoule into the hollow volume 24. It will be appreciated that ampoule interface that is deployable in the hollow volume 24 prior to insertion of ampoule is considered within the scope of the present invention.

Returning now to the Figures, the ampoule sheath 30 is configured with an inside surface having a diameter 34 equal to an outside diameter of the ampoule 40 and an outside surface having diameter 36 equal to an inside diameter of the hollow interior volume 24 of the syringe plunger 20. Configured thusly, the inside surface 34 interacts with an outside surface of the ampoule 40 and the outside surface 36 interacts with an inside surface of the hollow interior volume 24 of the syringe plunger 20.

Figure 5:
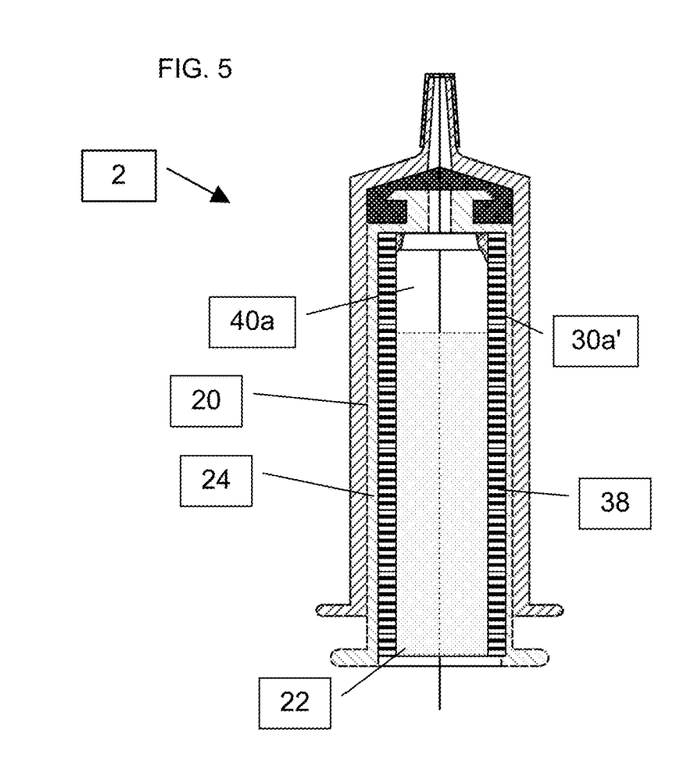
FIG. 5 is a longitudinal section view illustrating a first exemplar variation of the ampoule sheath of FIGS. 1A-2B.

Due to the numerous variations on sizes on medical ampoules, especially diameters, the syringe plunger 20 is manufactured such that the inside diameter of the hollow volume 24 is constant and the thickness of the wall 38 of the ampoule sheath 30 is varied to accommodate the size of the ampoule to be used. Therefore, the ampoule sheath 30 serves to adapt the size of the medical ampoule 40 to fit snugly into the generic size of the hollow volume 24. This first variation of the ampoule sheath 30a' is best illustrated in FIG. 5.

Figure 6:
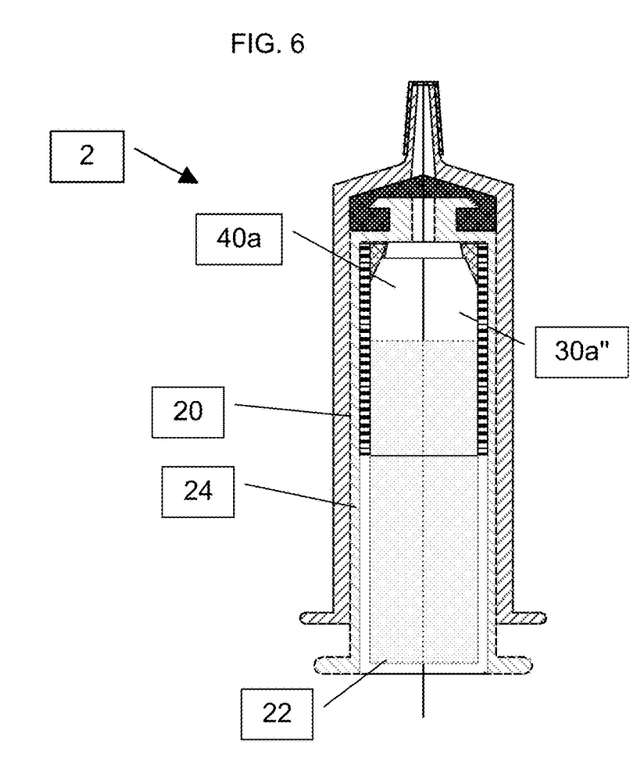
FIG. 6 is a longitudinal section view illustrating a second exemplar variation of the ampoule sheath of FIGS. 1A-2B.

A second variation of the ampoule sheath 30 is illustrated in FIG. 6. As seen here, the ampoule sheath 30a" does not extend the full length of the ampoule 40a.

Figure 3A:
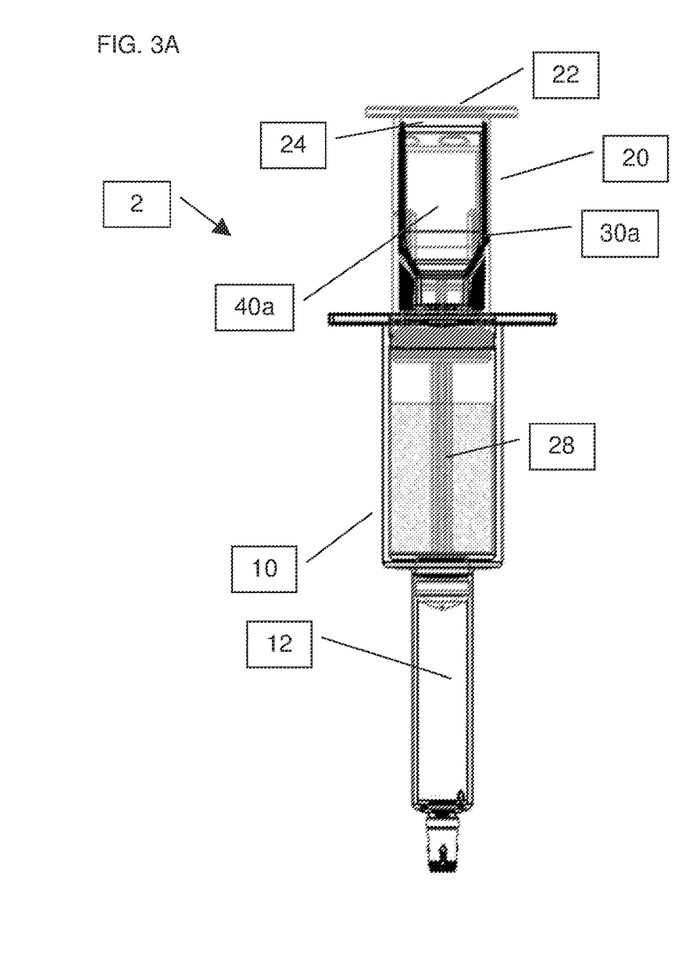
FIG. 3A is a longitudinal section view of a second preferred embodiment of a syringe constructed and operational according to the teaching of the present invention, shown here with an ampoule deployed in the plunger and the plunger pulled out of the syringe body.
Figure 3B:
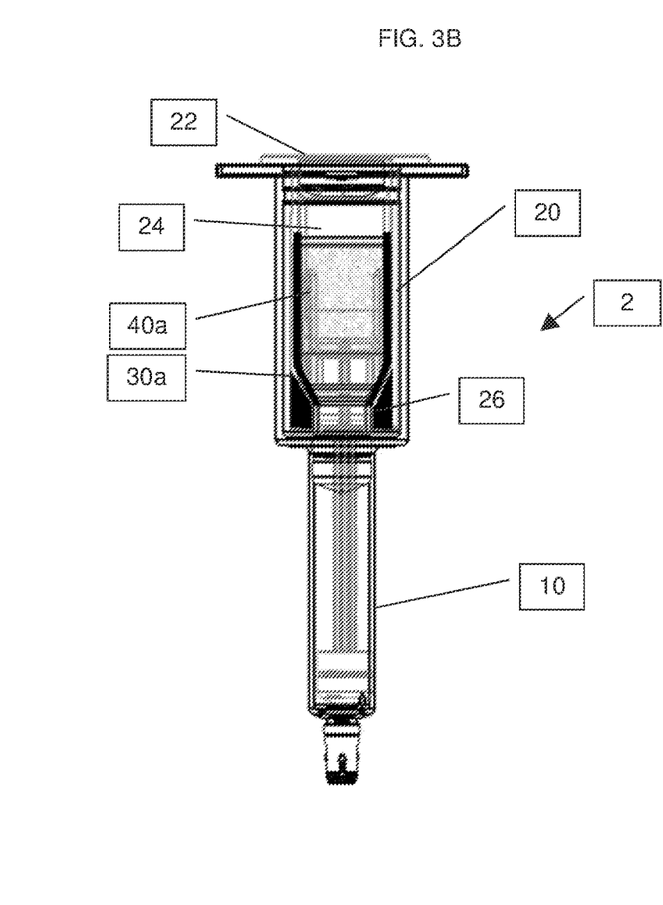
FIG. 3B is a longitudinal section view of the syringe of FIG. 3A, shown here with the plunger deployed in the syringe body.
Figure 4A:
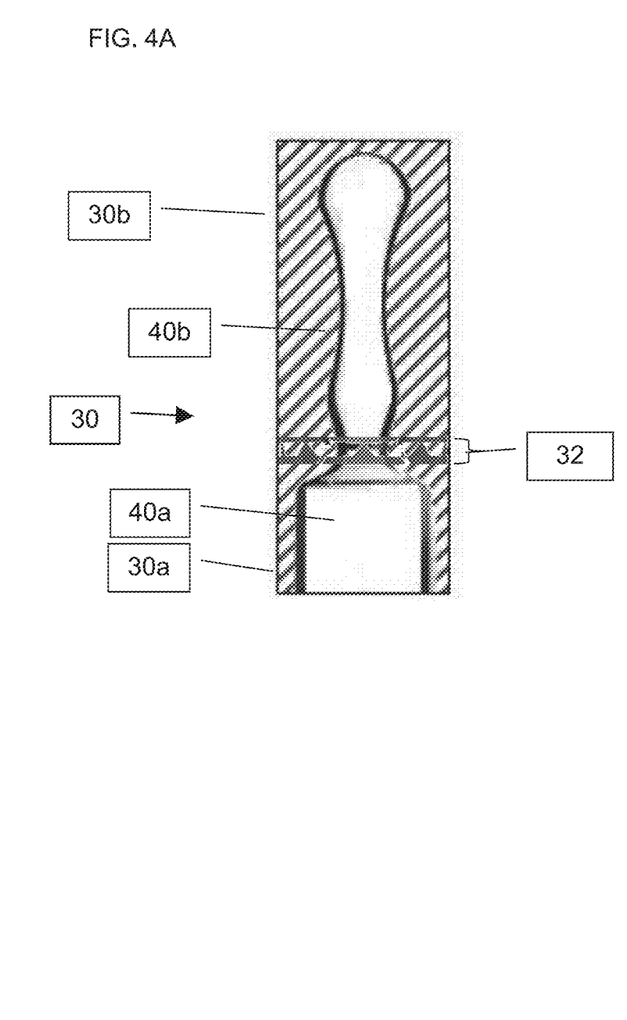
FIG. 4A is a longitudinal section view of a second preferred embodiment of an ampoule sheath constructed and operational according to the teaching of the present invention, shown here after deployment on a breaking ampoule but prior to breaking.
Figure 4B:
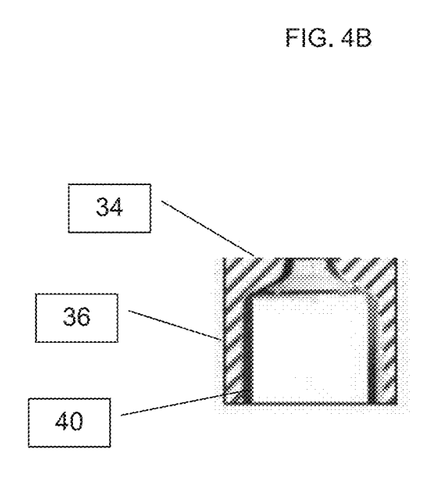
FIG. 4B is a longitudinal section view of the ampoule sheath of FIG. 4A, shown here is the portion of the ampoule sheath deployed on the ampoule after breaking the ampoule.

FIGS. 3A and 3B illustrate a second preferred embodiment of the syringe of the present invention. It will be understood that elements shown here that correspond to elements of the first preferred embodiment of FIGS. 2A and 2B are numbered the same. As illustrated here, the outside diameter 36 of the ampoule sheath 30a and the inside diameter of the hollow interior volume 24 of the syringe plunger 20 are complimentarily varied along their common length, so as to enhance the interface action by increasing friction between the ampoule sheath 30a and the surface of the hollow interior volume 24, and thereby provide a better fit between the two elements.

As shown herein, the variance in the inside diameter of the hollow interior volume is illustrated as a step change in area 26 of the syringe plunger. However, it should be understood that this illustration is not intended as a limitation to such a design and that substantially any variation of the outside diameter 36 of the ampoule sheath 30 and the inside diameter of the hollow interior volume 24 of the syringe plunger 20 along their common length is within the scope of the present invention.

It will be appreciated that the tip of the syringe barrel 12 is configure to receive a standard medical needle for injection of the medicine draw from the ampoule, as is well known in the art.

Due to the numerous variations on sizes on medical ampoules, especially diameters, the syringe together with the ampoule sheath may be provided to the user as a kit containing a syringe body, a syringe plunger configured with a generically sized hollow interior volume and a plurality of ampoule sheaths of varying sizes so as to accommodate use with a range of differing sizes of medical ampoules.

The steps for use of the syringe kit of the present invention are as follows:

Step 1—choose an ampoule sheath of the correct size for the medical ampoule to be used.

Step 2—deploy the ampoule sheath on the medical ampoule, generally by sliding the ampoule sheath ever the medical ampoule.

Step 3—break the breakaway top of the medical ampoule together with the top portion 30b of the ampoule sheath 30.

Step 4—insert the medicine containing bottom portion 40a, with the bottom portion 30a of the ampoule sheath still deployed thereon, into the hollow interior volume 24 of the plunger 20 with the open end of the ampoule facing into the hollow interior volume 24.

Step 5—draw the plunger 20 out of the syringe body so as to draw medicine from the ampoule into the barrel 12 of the syringe body.

Step 6—attach an injection needle to the tip of the barrel 12 of the syringe body.

Step 7—inject the medicine.

Figure 7:
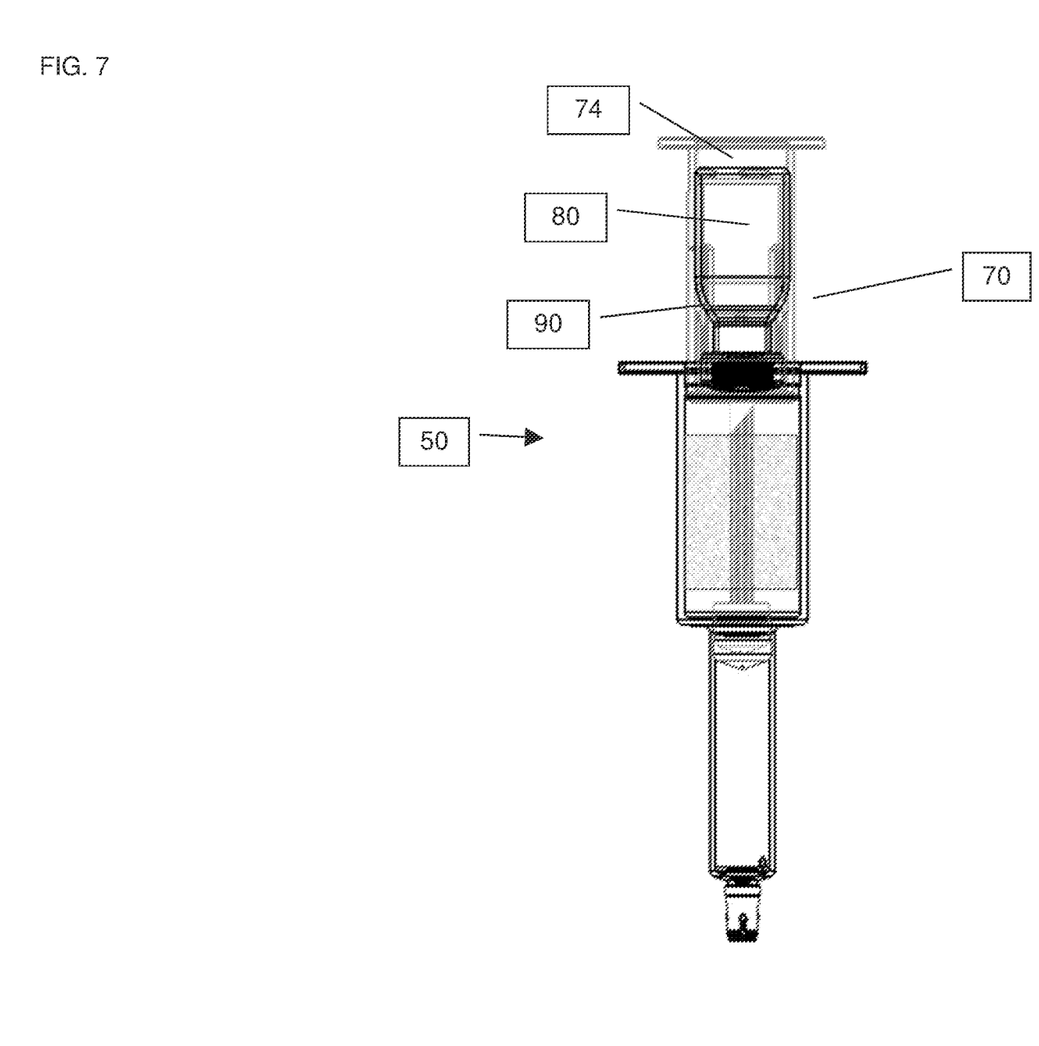
FIG. 7 is a longitudinal section view of a third preferred embodiment of a syringe constructed and operational according to the teaching of the present invention, in which a medical vial, upon which an ampoule sheath of the present invention is deployed, is deployed in the plunger of the syringe.

Regarding the numerous variations in size of medical vials in use today, the current state of the art is directed to devices that are dedicated to a particular size. Therefore, as illustrated in FIG. 7, the feature of the sheath, here a vial sheath 90, of this embodiment 50 of the present invention may be used to benefit as an interface element for adapting substantially any size medical vial 80 for use with the standardized diameter of the hollow interior volume 74 of the syringe plunger 70.

It will be readily understood that once the vial 80, with the vial sheath 90 deployed thereon, is inserted into the hollow interior volume 74 the operation of this embodiment is essentially the same as that of the embodiment of FIGS. 2A and 2B.

It will be appreciated that the above descriptions are intended only to serve as examples and that many other embodiments are possible within the spirit and the scope of the present invention.

What is claimed is:

1. A kit for the direct use of a variety of medical ampoules of differing sizes, with a syringe, the kit comprising:
    (a) a syringe body;
    (b) a syringe plunger configured for insertion into said syringe body, said syringe plunger having a hollow interior volume which is open at one end; and
    (c) a plurality of ampoule interface elements, each one of said plurality of ampoule interface elements being a sheath including:
        (i) a bottom portion,
        (ii) a top portion, and
        (iii) break lines intervening between said top portion and said bottom portion, such that said sheath is breakable along said break lines;
    wherein said sheath is adapted to be deployed, in a first state, over a respective corresponding ampoule of the variety of medical ampoules, such that said bottom portion is deployed on a medicine containing bottom portion of said respective corresponding ampoule and said top portion is deployed on a top breakaway portion of said respective corresponding ampoule,
    and in a second state, only said bottom portion being deployed over said medicine containing bottom portion of said respective corresponding ampoule, said top breakaway portion having been detached and discarded with said top portion;
    wherein each of said ampoule interface elements, in said second state, is adapted to be interchangeably received within said hollow interior volume and configured for deployment between an outer surface of a respective, corresponding ampoule of the variety of medical ampoules and a surface defining said hollow interior volume so as to hold said respective, corresponding ampoule in said hollow interior volume, each of said plurality of ampoule interface elements having an outside diameter sized to fit closely against an inside diameter of said hollow interior volume of said syringe plunger,
    wherein said plurality of ampoule interface elements includes at least: a first of said ampoule interface elements that has a first inside diameter for receiving a medical ampoule of a first size, and
    a second of said ampoule interface elements that has that has a second inside diameter different from said first inside diameter for receiving a medical ampoule of a second size.

2. The kit of claim 1, wherein each of said plurality of ampoule interface elements is configured to provide a seal between said respective, corresponding ampoule and said surface defining said inside diameter of said hollow interior volume of said syringe plunger.

3. The kit of claim 1, wherein said outside diameter of each of said plurality of ampoule interface elements and the inside diameter of said hollow interior volume of said syringe plunger are complimentarily varied along a common length, so as to enhance an interface action by increasing friction between them.

4. The kit of claim 1, wherein each of said plurality of ampoule interface elements is breakable and aids in a breaking process of breaking said respective corresponding ampoule prior to being received in said hollow interior volume; thereby providing added protection to a user during said breaking process.

5. The kit of claim 1, wherein said hollow interior volume of said syringe plunger is of a generic size and each of said plurality of ampoule interface elements serves to adapt a size of said respective corresponding ampoule to fit snugly within said generic size of said hollow interior volume.

6. A kit of ampoule interface elements for use holding one ampoule of a variety of medical ampoules in a hollow interior volume of a syringe plunger, the kit comprising:
 a plurality of ampoule interface elements, each one of said plurality of ampoule interface elements being a sheath including:
  (i) a bottom portion,
  (ii) a top portion, and
  (iii) break lines intervening between said top portion and said bottom portion, such that said sheath is breakable along said break lines;
  wherein said sheath is adapted to be deployed, in a first state, over the one ampoule when whole, and in a second state, only said bottom portion being deployed over a bottom portion of the one ampoule when a top portion thereof has been removed;
 wherein each of said ampoule interface elements, in said second state, is adapted to be interchangeably received within the syringe plunger and configured for deployment between an outer surface of the one ampoule and a surface defining the hollow interior volume so as to hold the medical ampoule in the hollow interior volume, each of said plurality of ampoule interface elements having an outside diameter sized to fit closely against an inside diameter of the hollow interior volume of the syringe plunger, wherein said plurality of ampoule interface elements includes at least a first of said ampoule interface elements that has a first inside diameter for receiving a medical ampoule of a first size selected from the variety of medical ampoules, and a second of said ampoule interface elements that has a second inside diameter different from said first inside diameter for receiving a medical ampoule of a second size selected from the variety of medical ampoules.

7. The kit of claim 6, wherein each one of said plurality of ampoule interface elements is configured for deployment on a respective corresponding medical ampoule of the variety of medical ampoules prior to insertion of said respective corresponding medical ampoule, with a respective ampoule interface element deployed thereon, into the hollow interior volume.

8. The kit of claim 6, wherein each of said plurality of ampoule interface elements is breakable and aids in a breaking process of the one ampoule thereby providing added protection to a user during said breaking process, said breaking process occurring prior to the one ampoule being received in said hollow interior volume.

9. A method of deploying a medical ampoule in a syringe, the method comprising:
 (a) providing a syringe body;
 (b) providing a syringe plunger configured for insertion into said syringe body, said syringe plunger having a hollow interior volume which is open at one end; and
 (c) providing a plurality of ampoule interface elements, each one of said plurality of ampoule interface elements being a sheath including:
  (i) a bottom portion,
  (ii) a top portion, and
  (iii) break lines intervening between said top portion and said bottom portion, such that said sheath is breakable along break lines;
  wherein said sheath is adapted to be deployed, in a first state, over the one ampoule when whole, and in a second state, only said bottom portion being deployed over a bottom portion of the one ampoule when a top portion thereof has been removed;
 wherein each said ampoule interface elements, in said second state, is adapted to be interchangeably received within said hollow interior volume and configured for deployment between an outer surface of a corresponding sized ampoule and a surface defining said hollow interior volume so as to hold said correspondingly sized ampoule in said hollow interior volume, each of said plurality of ampoule interface elements having an outside diameter sized to fit closely against an inside diameter of said hollow interior volume of said syringe plunger,
  wherein said plurality of ampoule interface elements includes at least: a first of said ampoule interface elements has a first inside diameter for receiving an ampoule of a first size, and a second of said ampoule interface elements has a second inside diameter different from said first inside diameter for receiving an ampoule of a second size;
 (d) deploying an appropriately sized one of said ampoule interface elements; and
 (e) insertion of the medical ampoule into said hollow interior volume such that said appropriately sized one of said ampoule interface element holds the medical ampoule therein.

10. The method of claim 9, further including the steps of:
 (f) deploying said appropriately sized one of said ampoule interface elements on the medical ampoule prior to breaking the medical ampoule;
 (g) breaking the medical ampoule; and
 (h) inserting only a medicine containing portion of the medical ampoule into said hollow interior volume with said bottom portion of said appropriately sized one of said ampoule interface elements still deployed thereon.

* * * * *